United States Patent [19]
Barnicki et al.

[11] Patent Number: 5,512,691
[45] Date of Patent: Apr. 30, 1996

[54] PROCESS FOR THE PRODUCTION OF TOCOPHEROL CONCENTRATES

[75] Inventors: Scott D. Barnicki; Charles E. Sumner, Jr.; H. Chip Williams, all of Kingsport, Tenn.

[73] Assignee: Eastman Chemical Company, Kingsport, Tenn.

[21] Appl. No.: 334,901

[22] Filed: Nov. 7, 1994

[51] Int. Cl.$^6$ .................................................. C07D 311/72
[52] U.S. Cl. ............................................................ 549/413
[58] Field of Search .............................................. 549/413

[56] References Cited

U.S. PATENT DOCUMENTS 2,432,181 12/1947 Trent.
3,153,055 10/1964 Brown et al..
3,335,154 8/1967 Smith.
4,454,329 6/1984 Takagi et al..

Primary Examiner—Nicky Chan
Attorney, Agent, or Firm—Bernard J. Graves; Harry J. Gwinnell

[57] ABSTRACT

Disclosed is an improved process for the preparation of tocopherol concentrates from vegetable oil distillates. Tocopherol concentrates are obtained containing 20–80% tocopherol by weight, with an overall recovery of tocopherol of 72% to 97%. The process is comprised first of an esterification reaction where the more volatile alcohols are converted to their less volatile fatty acid esters, followed by a series of distillation steps where components boiling higher and lower than the tocopherols are separated from tocopherols and other like boiling substances. Advantages of the process are that tocopherol concentrates are produced efficiently and economically in a minimum number of steps without the use of solvents and with a relatively small capital investment.

47 Claims, 2 Drawing Sheets

PROCESS FOR THE PRODUCTION OF TOCOPHEROL CONCENTRATES

FIELD OF THE INVENTION

This invention belongs to the field of organic chemistry. In particular, this invention relates to a process for the manufacture of tocopherol concentrates from the by-products of vegetable oil refining.

BACKGROUND OF THE INVENTION

Alpha, beta, gamma, and delta tocopherol (hereafter referred to as tocopherols) can be found in various ratios and concentrations in crude vegetable oils such as soy bean, sunflower, canola, rapeseed, cottonseed, safflower, corn, palm, palm kernel, and rice bran oil. These tocopherols are a valuable constituent of vegetable oil as they help prevent oxidation and spoilage. During the refining of vegetable oils a large fraction of the tocopherols are lost to various by-products and waste streams. These waste and by-products streams include, but are not limited to, deodorizer distillates, steam refining distillates, and acidulated soapstocks. The vegetable oil refining by-products typically contain from less than 1% to greater than 20% tocopherol by weight. The oil refining by-products are a valuable source of raw material for the production of natural vitamin E and other tocopherol antioxidants. However, the by-product streams also contain 20 to 99% by weight free fatty acids, less than 1% to 20% by weight sterols, less than 1% to 20% by weight sterol esters of fatty acid, less than 1% to 40% by weight mono, di, and triglycerides, less than 1% to 30% by weight hydrocarbons, and several percentage by weight of other compounds, in addition to tocopherols. Thus, in order to obtain a tocopherol concentrate stream useful for production of high purity vitamin E, it is necessary to remove these substances.

Numerous methods have been proposed for the recovery of tocopherols from vegetable oil refining by-products. For example, U.S. Pat. No. 2,432,181 teaches that tocopherols can be recovered from vegetable oils and fats by reacting the fatty acid glycerides with an aliphatic monohydric alcohol in the presence of an alkaline alcoholysis catalyst, followed by a flash distillation of residual alcohol glycerol, and fatty acid esters.

U.S. Pat. No. 3,153,055 teaches a process for the isolation of sterols and tocopherols from deodorizer distillate by esterification of free fatty acids and glycerides into lower monohydric alcohol esters under strongly acidic conditions. The sterols and tocopherols are fractionally extracted from the esterification product with a combination of polar and nonpolar solvents.

U.S. Pat. No. 3,335,154 teaches that deodorizer distillate can be saponified and acidulated to convert glycerides and sterol esters to free fatty acids and free alcohols (glycerol, sterols respectively). The free fatty acids are esterified with a monohydric lower alcohol and mineral acid catalyst. The sterols are precipitated/crystallized by the addition of water to the mixture, and the tocopherols are concentrated by removal of the fatty acid esters by molecular distillation.

All of the above processes suffer from serious drawbacks. They require the addition of extraneous monohydric alcohols and result in the production of fatty acid esters which are not normally present in the vegetable oil by-product feed material. The excess monohydric alcohol must be removed in an additional processing step. In order to produce a highly concentrated tocopherol product the sterols must either be removed by crystallization or by other means. Saponification requires large amounts of caustic and acid for acidulation, thereby creating excessive salt wastes.

U.S. Pat. No. 4,454,329 teaches that a tocopherol concentrate can be obtained from deodorizer distillates by esterification of the free fatty acids with a dihydric or polyhydric alcohol, in the presence or absence of an acid catalyst. The esterification is preferably carried out in the presence of an aromatic solvent such as benzene, toluene, or xylene. The esterified mixture is then subjected to either a solvent extraction or a molecular distillation to produce the final tocopherol concentrate. Preferably, the solvent extraction is proceeded by a hydrogenation to convert the unsaturated triglycerides into saturated triglycerides, thereby decreasing the solubility of the triglycerides in the solvent phase of the extraction. Distillation of the esterified mixture concentrates tocopherols, sterols, hydrocarbons and other components with similar boiling points in the distillate. The triglycerides and other high-boiling components are left in the distillation residue.

The above process is unsatisfactory for a number of reasons. Deodorizer distillates and the like typically contain a 1/1 to 3/1 ratio of sterols to tocopherols, depending on the vegetable oil source. The tocopherols and sterols have very similar boiling points and there-fore cannot be separated by distillation alone. The esterification is not run in such a fashion to ensure that the sterols are converted into sterol esters (which have a much higher boiling point than tocopherol). The distillate containing the tocopherols and sterols produced by the above process must be further treated by other separation techniques in order to produce a tocopherol concentrate essentially free of sterols.

In the solvent extraction version of the process, the solvent must be removed from the tocopherol extract, adding additional cost and complication to the process. The preferred embodiment of the solvent extraction, proceeded by the hydrogenation, adds still another step, with concomitant cost and complication. In addition, typical copper and nickel hydrogenation catalysts are known to be prooxidants, which promote the destruction of tocopherol, thereby lowering the yield of tocopherol from the process.

BRIEF DESCRIPTION OF THE DRAWINGS

FIGS. 1 and 2 are more fully described below.

SUMMARY OF THE INVENTION

Figure 1:
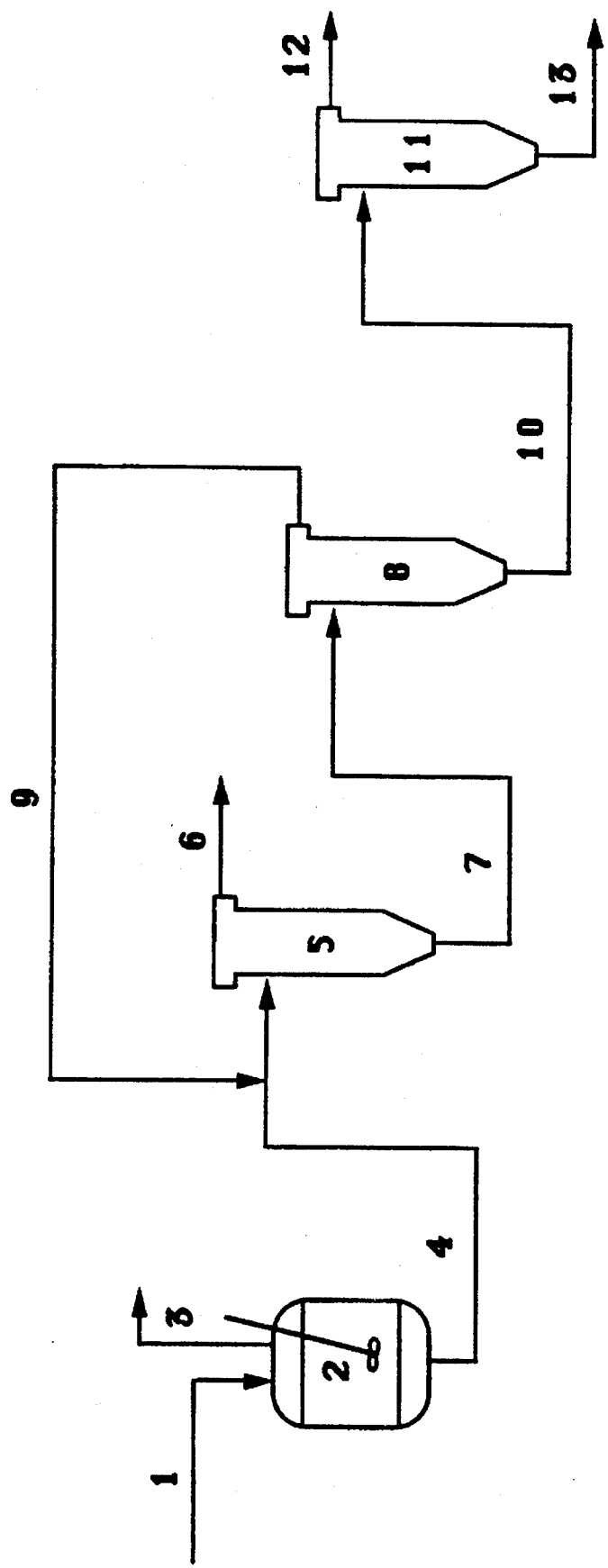
FIG. 1 is a diagram outlining one aspect of the method of the present invention, in which an esterification reaction is conducted in reactor (2), which is then subjected to a series of distillation steps (5), (8), and (9), to provide the desired tocopherol.

One object of this invention is to provide an efficient, economical process for the isolation of tocopherols from vegetable oil processing by-products. The raw material for the process can be deodorizer distillate, steam refining distillate, acidulated soapstock, or any other vegetable oil by-product containing typically from less than 1% tocopherol to upwards of 20% tocopherol by weight.

In this invention, the vegetable oil by-product is subjected to an esterification step, with or without an acid catalyst, in which the sterols react with the free fatty acid already present in the mixture to form high-boiling sterol esters. Any other alcoholic moieties, triterpenoid alcohols, methyl-sterols, and the like, are converted to high-boiling fatty acid esters and waxes. Moreover, any mono- and di-fatty acid glycerides are largely converted to triglycerides by reaction with the free fatty acids. The tocopherols also react to a limited extent; the extent of reaction can be controlled by proper selection of reaction time and temperature. The esterified mixture is then subjected to a series of distillation steps in which components boiling higher and lower than the tocopherols are separated from tocopherols and other like-boiling substances. The distillation steps consist of one or more separate distillation operations to remove unreacted free fatty acids overhead, along with any low-boiling compounds, from a tocopherol-rich bottoms product and one distillation operation to remove a tocopherol-rich product overhead from sterol esters, fatty acid polyesters of glycerol, waxes, and other high-boiling substances. Either the distillation operations to remove the fatty acid and low-boilers, or the distillation operation to remove the high-boilers may be done first. The resulting product of the process is a tocopherol concentrate comprised primarily of tocopherol and hydrocarbons with similar boiling points, which is essentially free of free fatty acids, sterols, sterol esters, fatty acid polyesters of glycerol, waxes, and other high-boiling compounds.

As a further aspect of this invention, the catalyst for the esterification step is a monoalkyl tin compound, zinc salt of an organic acid, titanium (IV) alkoxides, zinc oxide, phosphoric acid or other mild mineral acids.

DETAILED DESCRIPTION OF THE INVENTION

The present invention provides a method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides; and (b) followed by subjecting said mixture to a series of distillation operations comprising:

(i) one or more separate distillation operations, wherein said distillation(s) is (are) conducted at a temperature of about 200° C. to 320° C. and a pressure of about 0.01 torr to 10 torr, in series wherein unreacted fatty acids and low-boiling components are removed as a vapor effluent and a liquid effluent comprised of tocopherols is removed; and (ii) wherein said liquid effluent from step (b)(i) is subjected to one or more distillations in series, wherein said distillation(s) is (are) conducted at a temperature of about 170° C. to 270° C. and a pressure of about 0.005 torr to 2 torr, wherein a tocopherol concentrate is removed as a vapor effluent and wherein a liquid effluent comprised of sterol esters, fatty acid esters, glycerides, waxes, and other high-boiling substances is removed.

Figure 2:
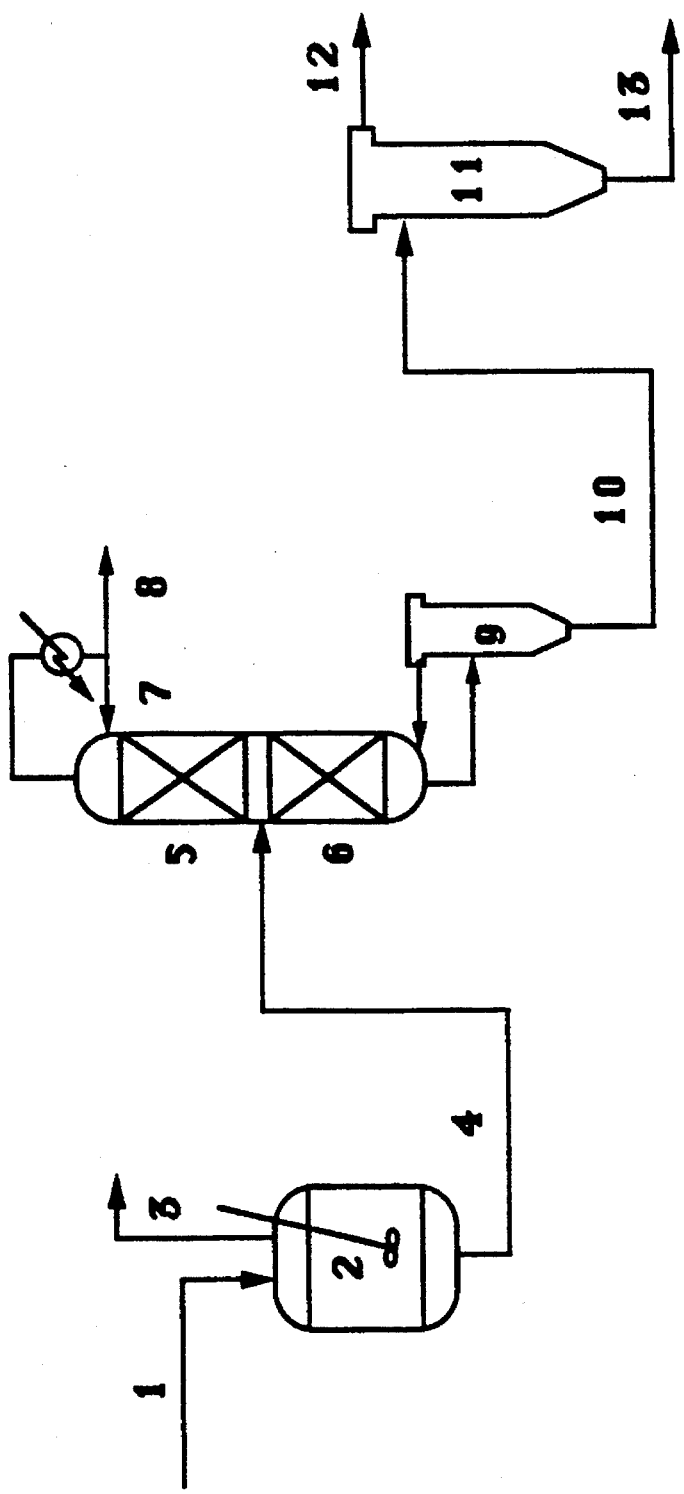
FIG. 2 is a diagram outlining the preferred method of the present invention, in which an esterification reaction is conducted in reactor (2), and subjected to two distillation steps.

The description of a preferred aspect of the present invention is made in reference to the process diagrams of FIGS. 1 and 2. The vegetable oil by-product is fed via line (1) to a stirred tank or batch reactor, unit (2), operating at a temperature of about 70°–300° C., preferably in the range of 150°–230° C., and at a pressure of about 50 torr to 760 torr, preferably about 100–200 torr. The residence time in the reactor is preferably from about 1 to 24 hours, most preferably 90 minutes to two hours in the presence of an acid catalyst, and from two hours to ten hours when no catalyst is used. Preferred catalysts include monoalkyl tin compounds, zinc salt of an organic acid, titanium (IV) alkoxides, zinc oxide, phosphoric acid and other mild mineral acids.

During the reaction step, the free fatty acid which is already present in the feed mixture reacts with the sterols to form high-boiling sterol esters and water. Any other alcoholic moieties, triterpenoid alcohols, methyl-sterols, and the like, also react with the free fatty acids to form high-boiling fatty acid esters, waxes, and water. Moreover, any mono- and di-fatty acid esters of glycerol are largely converted to triglycerides by esterification with the free fatty acids. The tocopherols also react to a limited extent with the free fatty acid to form tocopherol esters and water. The relative rates of the esterification reactions is glycerides>sterols>tocopherols. Thus, the reaction of tocopherols can be controlled by proper selection of reaction temperature and time. Tocopherol recovery from the reaction step is typically 80% to 97%, more typically 85% to 92%. Conversion of sterols to fatty acid sterol esters is typically 75% to 100%, more typically 85% to 95%. In a preferred embodiment, $C_{10}$–$C_{22}$ fatty acids are added to the starting material by-product, most preferably in an amount of up to about 40% by weight, based on the total weight of the by-product starting material.

The reactor is provided with a means for removal of the water of esterification, line (3). As is well-known in the art, the removal of the water of esterification drives the reaction equilibrium toward the formation of the fatty acid ester products.

The esterification product (4) is then subjected to a series of distillation steps in which components boiling higher and lower than the tocopherol are separated from tocopherol and other like-boiling substances. The distillation steps are one or more separate distillation operations to remove unreacted free fatty acids overhead along with any low-boiling compounds from a tocopherol-rich bottoms product, and one distillation operation to remove a tocopherol-rich product overhead away from sterol esters, fatty acid polyesters of glycerol, waxes, and other high-boiling compounds. Either the distillation operations to remove the fatty acid and low-boilers, or the distillation operation to remove the high-boilers may be done first. It should be understood that the reaction and distillation operations may be accomplished in batch, semi-batch, and continuous modes of operation.

This process produces tocopherol concentrates efficiently and economically in a minimum of steps. No extraneous substances are added to the raw material oil, except possibly an esterification catalyst and added $C_{10}$–$C_{22}$ fatty acids. No solvents or excess esterification alcohols need to be removed from the reaction product. The achievable tocopherol concentration in the final product is in the range of 20–80% tocopherol by weight, depending on the amount of hydrocarbons in the starting material. More typically the product will have a tocopherol concentration of 30–60% by weight of tocopherol. The overall recovery of tocopherol from the process is typically 72% to 97%, more typically 75% to 92%, most typically 80% to 85%.

One embodiment of the method of the present invention is illustrated by FIG. 1. The product (4) from the esterification step is distilled in unit (5) under high vacuum to remove a substantial fraction, typically 50–90%, more typically 60–80%, of the unreacted fatty acid along with a substantial fraction the low-boilers, stream (6), to leave a tocopherol-rich bottoms product (7). The distillation operation is conducted at temperatures and pressures such that the tocopherols are largely left in the bottoms product. The temperature and pressure of distillation operation (5) is in the range of 170° C. to 270° C., 0.05 to 10 torr. The preferred range is 200° C. to 240° C., 0.5 torr to 4 torr. The distillation apparatus (5) (as are all of the distillation equipment used herein) is preferably a high-vacuum design including a short path evaporator, a wiped-film evaporator, a centrifugal molecular still, or a falling film evaporator capable of low pressure operation.

The bottoms product (7) of the first distillation operation (5) is distilled a second time in distillation operation (8) under high vacuum to remove any remaining unreacted fatty acids and other low-boiling compounds. The temperature of distillation (8) must be higher or the pressure lower than distillation (5) in order to ensure essentially complete removal of any remaining fatty acids. The temperature and pressure of distillation (8) is in the range of 230° C. to 300° C., 0.01 to 5 torr. The preferred range is 240° C. to 280° C., 0.1 torr to 2 torr. Under these conditions a portion, typically 5–30%, of the tocopherols will distill overhead with the remaining fatty acids into stream (9), leaving an acid-free tocopherol-rich bottoms product (10). The distillate (9) containing some tocopherols and the remaining free fatty acid may be discarded or recycled to reactor (2) or the first distillation operation (5) in order to improve the overall yield of tocopherols. Since distillation (5) and distillation (8) are conducted under different temperature and pressure conditions, they act in combination as a multi-equilibrium staged device, lowering tocopherol losses and increasing fatty acid removal. The distillation apparatus (8) may be of any high-vacuum design including a short path evaporator, wiped-film evaporator, centrifugal molecular still, or falling film evaporator.

The tocopherol-rich bottoms product (10) of the second distillation (8) is then subjected to a third high-vacuum distillation (11). The tocopherol and other similarly boiling compounds are collected as a final tocopherol-rich distillate product (12). The triglycerides, sterol esters, other high-boiling fatty acid esters, and other high-boiling compounds are removed in the largely tocopherol-free bottoms (13) of the distillation. Tocopherol recovery to stream (12) is typically 95% to 100%, more typically 96% to 99.9%. The catalyst, if any were used, exits in the residue. The temperature and pressure of distillation operation (11) is in the range of 170° C. to 270° C., 0.005 to 2 torr. The preferred range is 200° C. to 250° C., 0.01 torr to 0.05 torr. The distillation apparatus (11) may be of any high-vacuum design including a short path evaporator, wiped-film evaporator, centrifugal molecular still, or falling film evaporator.

Thus, as a further aspect of the present invention, there is provided a method for preparing a tocopherol concentrate which comprises the steps:

(a) heating a vegetable oil by-product comprised of tocopherols, fatty acids, sterols, sterol esters of fatty acids, and mono-, di-, and triglycerides, said by-product optionally containing added $C_{10}$–$C_{22}$ fatty acids, optionally in the presence of an acid catalyst, at a temperature of about 70° to 300° C. and a pressure of about 50 torr to 760 torr, while continuously removing water formed thereby, to form a mixture comprised of sterol esters, high boiling fatty acid esters, waxes, and glycerides;

(b) followed by subjecting said mixture to distillation at a temperature of about 170° C. to 270° C. and a pressure of about 0.05 to 10 torr, while removing unreacted fatty acids and low-boiling components as a vapor effluent and a liquid effluent comprised of tocopherols;

(c) followed by subjecting the liquid effluent from step (b) to distillation at a temperature of about 230° C. to 300° C. and a pressure of about 0.01 to 5 torr, while removing remaining fatty acids and approximately 5 to 30 percent of total tocopherols as a vapor effluent and a liquid effluent which is a tocopherol-enriched product; and (d) followed by subjecting the liquid effluent from step (c) to distillation at a temperature of about 170° C. to 270° C. and a pressure of about 0.005 to 2 torr, and collection and isolation of a tocopherol concentrate as a vapor effluent.

As noted above, preferred apparatus for the distillation steps include any high-vacuum design including a short path evaporator, wiped-film evaporator, centrifugal molecular still, or falling film evaporator. Accordingly, as a further aspect of the present invention, there is provided a method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:
  a first distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr,
  wherein a vapor effluent comprised of a substantial fraction of the unreacted free fatty acids, and low-boiling materials is removed,
  wherein a liquid effluent which is comprised of a tocopherol-enriched mixture is removed;

(c) followed by feeding the liquid effluent from step (b) to a second distillation zone comprising:
  a second distillation apparatus selected from the group consisting of a short path evaporator, a wiped film evaporator, a centrifugal molecular still, and a falling film evaporator, operated at a about 240° C. to 280° C. and a pressure of 0.01 to 2 torr,
  wherein a vapor effluent comprised of remaining fatty acids and approximately 5 to 30 percent of total tocopherols is removed,
  wherein a liquid effluent comprised of a tocopherol-enriched mixture is removed; and (d) followed by feeding the liquid effluent from step (c) to a third distillation zone comprising:

a third distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr, wherein a vapor effluent which is a tocopherol concentrate is removed and isolated.

It should be appreciated that the order of the fatty acid removal and high-boilers distillation may be reversed, i.e., steps (b) and (d) of the above aspects of the invention would be reversed. In this embodiment, the product of the esterification reactor (4) is fed first to distillation operation (11). The free fatty acids, low-boilers and tocopherols are distilled overhead first from the sterol esters, fatty acid polyesters of glycerol, waxes, and other high-boiling compounds. The tocopherol-rich distillate is then fed to distillation operation (5) to remove a substantial fraction of the fatty acids and low-boilers and then to distillation operation (8) to remove the remaining fatty acids and low-boilers. The final tocopherol-rich concentrate is the bottoms product of distillation operation (8). The distillate of unit (8) may be recycled to the reactor (2), the first distillation (11), or the second distillation (5) in order to increase the overall tocopherol recovery.

A more highly preferred embodiment of present invention is illustrated by FIG. 2. The vegetable oil by-product (1) is esterified in a batch or continuous reactor (2), with or without catalyst. The water of esterification is removed continuously via line (3) during the reaction. The product of the esterification step (4) is distilled under high vacuum to remove essentially all of the unreacted fatty acid, typically 90% to 99.9%, more typically 97% to 99.9%, along with a substantial fraction of other low-boilers via stream (8) to leave a tocopherol-rich bottoms product (10). The temperature and pressure of the distillation is in the range of 220° C. to 320° C., 0.1 to 8 torr. The preferred range is 260° C. to 290° C., 0.5 torr to 4 torr. In the preferred embodiment of the invention, the distillation apparatus for the fatty acid removal step is a multistage, refluxed fractionating column. The column must contain at least one, preferably two to four, equilibrium stages of rectification (5), as well as an optional stripping section (6). The column must also have the capability of providing reflux via line (7) to the rectification section (5). The fractionating capability of the device greatly decreases the tocopherol loss to the distillate to typically less than 5%, more typically 0.2% to 2.0%, and increases the removal of the free fatty acid from the bottoms product. The optional stripping section further increases the removal of the free fatty acids from the bottoms product. The extent of tocopherol loss is highly dependent on the reflux ratio, defined as the ratio of the mass flow rate of stream (7) to the mass flow rate of stream (8). In the preferred embodiment of the invention the reflux ratio is in the range of 0.3 to 5.0, more preferably from 0.5 to 2.0. The staging in the rectification and optional stripping sections may be provided by any vapor-liquid contacting device, including bubble cap trays, sieve trays, random packing, and structured packing. In the preferred embodiment of the invention, the equilibrium staging is provided by high efficiency, low pressure drop structured packing, in order to lower residence time and reduce the temperature required for distillation. The reboiler of the distillation apparatus may be of any high-vacuum, low residence design including a short path evaporator, wiped-film evaporator, centrifugal molecular still, or falling film evaporator.

The tocopherol-rich bottoms product (10) of the first distillation is then subjected to a second high-vacuum distillation (11). The tocopherol and other similarly boiling compounds are collected as a tocopherol-rich distillate product (12). The triglycerides, sterol esters, other high-boiling fatty acid esters, and other high-boiling compounds are removed in the largely tocopherol-free bottoms, stream (13), of the distillation. Tocopherol recovery to stream (12) is typically 95% to 100%, more typically 96% to 99.9%. The catalyst, if any were used, exits in the residue. The temperature and pressure of the second distillation is in the range of 170° C. to 300° C., 0.005 to 2 torr. The preferred range is 200° C. to 250° C., 0.01 torr to 0.05 torr. The distillation apparatus (11) may be of any high-vacuum design including a short path evaporator, wiped-film evaporator, centrifugal molecular still, or falling film evaporator.

Thus, as a further aspect of the present invention, there is provided a method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:

a first distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids and low-boiling materials is removed; and wherein a liquid effluent which is comprised of a tocopherol-enriched mixture is removed;

(c) followed by feeding the liquid effluent from step (b) to a second distillation zone comprising:

one or more separate distillation apparatus in series selected from the group consisting of a short path evaporator, a wiped film evaporator, a centrifugal molecular still, and a falling film evaporator, operated at a temperature of about 200° C. to 320° C. and a pressure of about 0.01 torr to 10 torr, wherein a liquid effluent comprised of sterol esters, fatty acid esters, glycerides, waxes, and other high-boiling materials is removed;

wherein a vapor effluent which is a tocopherol concentrate is removed and isolated.

It should also be understood that the order of the fatty acid removal and high-boilers distillation may be reversed in this embodiment. In this embodiment, the product of the esterification reactor (4) is fed first to distillation operation (11). The free fatty acids, low-boilers and tocopherols are distilled overhead first from the sterol esters, fatty acid polyesters of glycerol, waxes, and other high-boiling compounds. The tocopherol-rich distillate is then fed to a multi-staged fractionating distillation operation to remove essentially all of the fatty acids and a substantial fraction of the low-boilers. The distillation operation consists of a refluxed rectifying section (5), a reboiler (9), and an optional stripping section (6). The final tocopherol-rich concentrate is the bottoms product of the second multi-staged distillation operation.

Acccordingly, as a further aspect of the present invention, there is provided a method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$-$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:
  one or more separate distillation apparatus in series selected from the group consisting of a short path evaporator, a wiped film evaporator, a centrifugal molecular still, and a falling film evaporator, said apparatus operated at a temperature of about 200° C. to 320° C. and a pressure of about 0.01 torr to 10 torr,
  wherein a liquid effluent comprised of sterol esters, fatty acid esters, glycerides, waxes, and other high-boiling materials is removed; and
  wherein a vapor effluent comprised of a tocopherols, free fatty acids and low-boilers is removed;

(c) followed by feeding the vapor effluent from step (b) to a second distillation zone comprising:
  a distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr,
  wherein a vapor effluent which is comprised of free fatty acids, and low-boiling materials is removed;
  wherein a liquid effluent which is a tocopherol concentrate is removed and isolated.

EXAMPLES

Example 1

A one liter 3-neck flask equipped with a mechanical stirrer, heating mantle, Dean-Stark trap, reflux condenser, $N_2$ inlet, and thermowell was charged with 500 g of soy oil deodorizer distillate and 0.5 g of zinc acetate. The resulting mixture was stirred and heated for three hours at 230° C. A nitrogen flow of 250 mL/min was bubbled through the mixture while it was heated. The mixture was sampled and analyzed for tocopherols, sterols, sterol esters, fatty acids, and glycerides. The results are listed in Table 1.

Example 2

The procedure outlined above was followed except that 500 g of canola oil deodorizer distillate was charged to the reactor and 0.25 g of butylstannoic acid was used as the catalyst. The results are shown in Table 2.

Example 3

The procedure outlined in example 1 was followed except that 1.8 g of phosphoric acid was used as the catalyst. The results are shown in Table 3.

Example 4

The procedure outlined in example 1 was followed except that no catalyst was added. The mixture was stirred and heated for 24 hours at 170° C. The results are listed in Table 4.

Example 5

The procedure outlined above was followed except that the reactor was charged with 500 g of sunflower deodorizer distillate. No catalyst was added. The mixture stirred and heated for three hours at 210° C. The results are listed in Table 5.

Example 6

The effect of temperature on reaction rates was examined using the same reactor equipment as outlined in example 1. The reactor was charged with 500 g of soy deodorizer distillate for each run at 132° C., 150° C., and 170° C. No catalyst was added. Each mixture was stirred and heated for 19–20 hours and maintained at temperature. The results are listed in Table 6.

Example 7

A 150 gal stainless steel reactor equipped with an anchor agitator, steam jacket, nitrogen inlet, vacuum system, and outlet pipe for water removal was charged with approximately 800 lb of canola oil deodorizer distillate for each of four reactor runs. For each run the vacuum was set at 200 mm Hg and the mixture was agitated and steam applied to the heating jacket during a three-hour heat-up to 210° C. The reactor was held at 210° C. and 200 mm Hg, with agitation, for two hours. The reactor was then rapidly cooled to below 100° C. Water of esterification was collected during the heat-up and hold times. The reactor product of each run was sampled and analyzed for tocopherols and sterols. The results for each of the four reactor runs are listed in Table 7.

Example 8

A 150 gal stainless steel reactor equipped with an anchor agitator, steam jacket, nitrogen inlet, vacuum system, and outlet pipe for water removal was charged with 310.8 lb of soy oil deodorizer distillate. No catalyst was added. The vacuum was set at 200 mm Hg and the mixture was agitated and steam applied to the heating jacket during a five-hour heat-up to 210° C. The reactor was held at 210° C. and 200 mm Hg, with agitation, for two and a half hours. The reactor was then rapidly cooled to below 100° C. Water of esterification was collected during the heat-up and hold times. The reactor product was sampled at 5 hours and 7.5 hours and analyzed for tocopherols and sterols. The results are listed in Table 8.

Example 9

A one liter 3-neck flask equipped with a mechanical stirrer, heating mantle, Dean-Stark trap, reflux condenser, $N_2$ inlet, and thermowell was charged with 500 g of soy triglycerides, 5.1 g of mixed soy tocopherols, and 0.5 g of dibutyl tin oxide. The resulting mixture was stirred and heated for two hours at 230° C. A nitrogen flow of 250 mL/min was bubbled through the mixture while it was heated. The mixture was sampled at one hour intervals and analyzed for tocopherols. The results are listed in Table 9.

Example 10

Referring to FIG. 1, distillation operation 5, soy deodorizer distillate was fed continuously to a single-stage 0.42 m2 thin film evaporator unit operating at 1.3 to 1.4 torr. The unit was heated by a hot oil system to a constant temperature of 238° C. The flow rate to the column was varied and timed samples of the distillate and bottoms products were collected. The flow rates of the distillate and bottoms streams were calculated from the masses of the timed samples, and a portion of each sample was analyzed for tocopherol and fatty acid content. The effect of flow rate on fatty acid removal and tocopherol recovery in the residue is shown in Table 10.

Example 11

The effect of temperature on fatty acid removal and tocopherol recovery in the residue was examined using the same thin film evaporator as outlined in example 11.

System pressure varied from 2.2 torr to 2.8 torr. Timed samples were collected to calculate distillate and bottoms rates and a portion of each sample was analyzed for tocopherol and fatty acid content. The results are shown in Table 11.

Example 12

A tocopherol-rich bottoms product resulting from the removal of a substantial fraction of the fatty acids was fed continuously to a 0.42 m2 short path evaporator unit operated at 0.05 to 0.099 torr. The temperature was varied from 239° C. to 279° C. and timed samples of the distillate and bottoms products were collected. The flow rates of the distillate and bottoms streams were calculated from the masses of the timed samples, and a portion of each sample was analyzed for tocopherol and fatty acid content. The effect of temperature on tocopherol recovery in the distillate is shown in Table 12.

Example 13

An one-inch diameter glass distillation column was equipped with a vacuum pump, refluxing distillation head, reflux ratio controller, metered feed pump, heated feed line, heated feed tank, and collection vessels for the distillate and bottoms products. The column consisted of a rectification section containing six inches of structured packing, a stripping section containing 18 inches of structured packing, and a reboiler section containing twelve inches of ⅛ inch spherical glass beads. The reboiler was fitted with a brass block heater, and the rectification and stripping sections were wrapped with heat tape and insulated.

A portion of the esterified canola deodorizer distillate from example 7 was fed continuously to the column at a rate of 300 ml/hr, while the reboiler temperature was varied from 240° C. to 300° C. and the reflux ratio from 0.33 to 2.00. The pressure at the top of the column was maintained at 0.7 torr and all column heat tapes at 220° C. At each reboiler temperature and reflux ratio setting the column was allowed to come to equilibrium and samples of the distillate and bottoms streams were collected and analyzed for fatty acids and tocopherols. The results are shown in Table 14.

Example 14

The esterified sunflower deodorizer distillate from Example 5 was fed continuously at a rate of 400 ml/hr to a single-staged 6-inch wiped film still equipped with a heating mantle, feed pump, high vacuum pump, and distillate and residue receivers. The still was maintained at a pressure of 0.1 torr and a temperature of 240° C. throughout the distillation. The distillate and bottoms product were collected and analyzed for fatty acids, tocopherols, sterols, sterol esters, and glycerides. Essentially all of the fatty acid (98.6% of that in the feed) and 78% of the tocopherol was recovered to the distillate product.

Example 15

[ASPEN™ run] Esterified soy deodorizer distillate containing 34% fatty acids, 8.5% tocopherols, 9% hydrocarbons, and 40% glycerides, sterol esters, and other heavy esters is fed continuously to a three-step distillative purification system as depicted in FIG. 1. The first single-staged high vacuum still is operated at 202° C. and 2.0 torr, the second single-staged high vacuum still at 235° C., 1.2 torr, and the third single-staged high vacuum still at 220° C., 0.01 torr. The distillate product of the second still is recycled to the feed of the first still in order to increase the recovery of the tocopherol. Aspen™ computer program simulated results are shown in Table 15. Overall recovery of tocopherol was 91%, with a concentration of 32% tocopherol.

Example 16

A portion of the esterified soy deodorizer distillate from Example 8 was fed continuously to the multi-staged refluxed column described in Example 14 at a rate of 300 ml/hr, top pressure of 0.7 torr, reboiler temperature of 285° C. and reflux ratio of 2.00. The distillate and bottoms product were collected and analyzed for fatty acids, tocopherols, sterols, and sterol esters. Recovery of tocopherol to the bottoms product of the first distillation step was 99.3%. Next, the tocopherol-rich bottoms product was fed continuously to the wiped film evaporator described in example 14 at a rate of 300 ml/hr, system pressure of 0.05 torr, and temperature of 235° C. The distillate and bottoms product of this second distillation were collected and analyzed for fatty acids, tocopherols, sterols, and sterol esters. Recovery of tocopherol to the distillate product of the second distillation step was 96.2%. Overall recovery of tocopherol through both distillation steps was 95.5%. Further results are given in Table 16.

Example 17

A portion of the esterified soy deodorizer distillate from Example 8 was fed continuously to the wiped film evaporator described in Example 14 at a rate of 300 ml/hr, system pressure of 0.05 torr, and temperature of 235° C. The distillate and bottoms product were collected and analyzed for fatty acids, tocopherols, sterols, and sterol esters. Recovery of tocopherol to the distillate product of the first distillation step was 73.3%. Next, the tocopherol-rich distillate product was fed continuously to the multi-staged refluxed column described in example 14 at a rate of 300 ml/hr, top pressure of 0.7 torr, reboiler temperature of 285° C. and reflux ratio of 2.00. The distillate and bottoms product of this second distillation were collected and analyzed for fatty acids, tocopherols, sterols, and sterol esters. Recovery of tocopherol to the bottoms product of the second distillation step was 98.8%. Overall recovery of tocopherol through both distillation steps was 72.4%. Further results are given in Table 17.

Example 18

A portion of the esterified canola deodorizer distillate from Example 7 was fed continuously to the wiped film evaporator described in Example 14 at a rate of 335 ml/hr, system pressure of 0.01 torr, and temperature of 235° C. The distillate and bottoms product were collected and analyzed for fatty acids, tocopherols, sterols, and sterol esters. Recovery of tocopherol to the distillate product of the first distillation step was 84%. Next, the tocopherol-rich distillate product was fed continuously to the multi-staged refluxed column described in example 14 at a rate of 346 ml/hr, top pressure of 2.5 torr, reboiler temperature of 260° C. and reflux ratio of 0.33. The distillate and bottoms product of this second distillation were collected and analyzed for fatty acids, tocopherols, sterols, and sterol esters. Recovery of tocopherol to the bottoms product of the second distillation step was 84.6%. Overall recovery of tocopherol through both distillation steps was 71.0%. Further results are given in Table 17.

TABLE 1

Esterification of Soy Deodorizer Distillate

Temperature: 230° C.
Pressure: 1 atm
Charge of oil: 500 g

| Reference No. | Time (min) | $Zn(OAc)_2$ | Tocopherols (g) | Sterols (g) | Sterol Esters (g) | Free Fatty Acids (g) | Monoglycerides (g) | Diglycerides (g) |
|---|---|---|---|---|---|---|---|---|
| 1 | 0 | 0.5 | 38.7 | 42.6 | 43.7 | 184.6 | 5.5 | 39 |
| 2 | 30 |  | 38.3 | 10.4 | 105.6 | 142.0 | 1.5 | 28.5 |
| 3 | 60 |  | 36.5 | 5.0 | 120.2 | 127.8 |  |  |
| 4 | 90 |  | 33.8 | 2.2 | 121.0 | 113.6 | >0.5 | 15 |
| 5 | 120 |  | 31.0 | 0.8 | 124.9 | 113.6 |  |  |
| 6 | 180 |  | 25.2 | 0.0 | 124.6 | 99.4 | >0.5 | 11.5 |

TABLE 2

Esterification of Canola Deodorizer Distillate

Temperature: 230° C.
Pressure: 1 atm
Charge of oil: 500 g

| Reference No. | Time (min) | Butyl Stannoic Acid (g) | Tocopherols (g) | Sterols (g) | Sterol Esters (g) | Free Fatty Acids (g) | Monoglycerides (g) | Diglycerides (g) |
|---|---|---|---|---|---|---|---|---|
| 7 | 0 | 0.25 | 35.5 | 39.2 | 26.5 | 241.4 | 48.5 | 31 |
| 8 | 30 |  | 33.1 | 15.8 | 109.0 | 170.4 | 3.5 | 14.5 |
| 9 | 60 |  | 31.7 | 5.7 | 126.2 | 156.2 |  |  |
| 10 | 90 |  | 30.3 | 2.3 | 139.5 | 156.2 | 4.0 | 8.5 |
| 11 | 120 |  | 28.7 | 1.0 | 142.0 | 142.0 |  |  |
| 12 | 180 |  | 25.2 | 1.1 | 144.5 | 142.0 | 3.5 | 5.5 |

TABLE 3

Esterification of Soy Deodorizer Distillate

Temperature: 230° C.
Pressure: 1 atm
Charge of oil: 500 g

| Reference No. | Time (min) | Phosphoric acid (g) | Tocopherols (g) | Sterols (g) | Sterol Esters (g) | Free Fatty Acids (g) | Triglycerides (g) |
|---|---|---|---|---|---|---|---|
| 13 | 0 | 1.8 | 38.7 | 42.6 | 43.7 | 184.6 |  |
| 14 | 30 |  | 36.9 | 6.7 | 105.4 | 151.2 | 107.5 |
| 15 | 60 |  | 34.4 | 1.8 | 119.4 | 137.2 |  |
| 16 | 90 |  | 31.4 | 0.0 | 122.0 | 128.8 | 135 |
| 17 | 120 |  | 28.6 | 0.4 | 125.8 | 123.2 |  |
| 18 | 180 |  | 22.3 | 0.4 | 121.3 | 114.8 | 260 |

TABLE 4

Esterification of Soy Deodorizer Distillate

Temperature: 170° C.
Pressure: 1 atm
Charge of oil: 500 g    no catalyst

| Reference No. | Time (min) | Tocopherols (g) | Sterols (g) | Sterol Esters (g) | Free Fatty Acids (g) | Monoglycerides (g) | Diglycerides (g) | Triglycerides (g) |
|---|---|---|---|---|---|---|---|---|
| 19 | 0 | 39.1 | 41.8 | 53.2 | 184.8 | 7.5 | 32.5 | 67.5 |
| 20 | 60 | 38.4 | 32.6 | 66.7 | 170.8 | 5.5 | 35 | 79 |
| 21 | 120 | 37.9 | 25.8 | 76.7 | 165.2 | 3.5 | 36 | 95 |
| 22 | 240 | 37.5 | 17.6 | 99.5 | 148.4 | 2.5 | 34.5 | 100 |
| 23 | 360 | 37.7 | 12.1 | 113.0 | 138.9 | 2.5 | 31.5 | 110 |
| 24 | 480 | 37.7 | 8.8 | 115.5 | 133.0 | 2.0 | 29 | 115 |
| 25 | 1440 | 35.9 | 1.5 | 138.1 | 106.4 | 0.0 | 14.5 | 150 |

TABLE 5

Esterification of Sunflower Deodorizer Distillate

Temperature: 210° C.
Pressure: 1 atm
Charge of oil: 500 g    no catalyst

| Reference No. | Time (min) | Tocopherols (g) | Sterols (g) | Sterol Esters (g) | Free Fatty Acids (g) | Triglycerides (g) |
|---|---|---|---|---|---|---|
| 26 | 0 | 11.5 | 8.8 | 36.1 | 211.7 | 20 |
| 27 | 30 | 11.7 | 4.0 | 48.1 | 199.1 | 116 |
| 28 | 60 | 11.8 | 2.0 | 53.3 | 196.0 | |
| 29 | 90 | 11.6 | 0.9 | 54.3 | 189.8 | 160 |
| 30 | 120 | 11.6 | 0.6 | 55.1 | 187.6 | |
| 31 | 180 | 11.4 | 0.0 | 57.1 | | 165 |

TABLE 6

Effect of Temperature on Esterification of Soy Deodorizer Distillate

Pressure: 1 atm
Charge of oil: 500 g at each temperature point    no catalyst

| Reference No. | Temperature (°C.) | Time (hr) | Tocopherols (g) | Sterols (g) | Sterol Esters (g) | Free Fatty Acids (g) | Triglycerides (g) |
|---|---|---|---|---|---|---|---|
| Starting Material | — | — | 39.2 | 42.5 | 47.5 | 196.0 | 69.0 |
| 32 | 170 | 19 | 36.2 | 2.1 | 140.9 | 112.0 | 135.0 |
| 33 | 150 | 19 | 36.9 | 12.0 | 119.8 | 109.2 | 110.0 |
| 34 | 132 | 20 | 39.7 | 17.7 | 102.1 | 151.2 | 80.5 |

TABLE 7

Esterification of Canola Deodorizer Distillates

Pressure: 200 torr
no catalyst

| Reference No. | Temperature (°C.) | Time (hr) | Start Tocopherol | End Tocopherol | Tocopherol Recovery | Starts Sterols | End Sterols |
|---|---|---|---|---|---|---|---|
| canola 86 | 210 | 2.0 hr hold | 6.9 | 6.7 | 97.1% | 12.14 | 0.97 |
| canola 92 | 210 | 2.0 hr hold | 6.4 | 5.94 | 92.8% | 10.98 | 0.91 |
| canola 95 | 210 | 2.0 hr hold | 7.08 | 6.46 | 91.2% | 11.91 | 0.84 |
| canola 98 | 210 | 2.0 hr hold | 6.78 | 6.19 | 91.3% | 11.43 | 0.42 |

TABLE 8

Esterification of Soy Deodorizer Distillates

Pressure: 200 torr
no catalyst

| Reference No. | Temperature (°C.) | Time (hr) | Start Tocopherol | End Tocopherol | Tocopherol Recovery | Starts Sterols | End Sterols |
|---|---|---|---|---|---|---|---|
| Brazilian soy | 190 | 5 hr sample | 11.1 | 8.66 | 78% | 4.0 | 0.18 |
| Brazilian soy | 210 | 7.5 hr sample | 11.1 | 7.43 | 67% | 4.0 | 0.0 |

TABLE 9

Equilibration of Mixed Tocopherols with Triglycerides

Temperature: 230° C.
Pressure: 1 atm
Reactor Charge: 500 g triglycerides, 5,1 g mixed soy tocopherols
Catalyst Charge: 0.5 g dibutyl tin oxide

| Reference No. | time (hr) | Tocopherol (g) |
|---|---|---|
| 35 | 0 | 5.1 |
| 36 | 1 | 2.0 |
| 37 | 2 | 1.9 |

TABLE 10

Effect of Feed Flowrate on Single-Staged Thin Film Distillation of Soy Deodorizer Distillate

| Run No. | System Pressure (torr) | Hot Oil Temperature °C. | Feed Rate (kg/hr) | Distillate Rate (kg/hr) | Distillate to Feed Ratio | Fatty Acid Yield to Distillate % | Tocopherol Yield to Residue % |
|---|---|---|---|---|---|---|---|
| 38 | 1.4 | 238 | 176 | 50.4 | 0.29 | 60 | 94 |
| 39 | 1.4 | 238 | 146 | 51.7 | 0.35 | 73 | 92 |
| 40 | 1.3 | 238 | 132 | 49.6 | 0.38 | 77 | 91 |
| 41 | 1.3 | 238 | 127 | 49.1 | 0.39 | 81 | 89 |

TABLE 11

Effect of Temperature on Single-Staged Thin Film Distillation of Soy Deodorizer Distillate

| Run No. | System Pressure (torr) | Hot Oil Temperature °C. | Feed Rate (kg/hr) | Distillate Rate (kg/hr) | Distillate to Feed Ratio | Fatty Acid Yield to Distillate % | Tocopherol Yield to Residue % |
|---|---|---|---|---|---|---|---|
| 42 | 2.2 | 249 | 120 | 54.2 | 0.45 | 90 | 83 |
| 43 | 2.8 | 264 | 117 | 58.0 | 0.495 | 95 | 75 |

TABLE 12

Effect of Temperature on Short Path Distillation of Residue from Example 10, 11

| Run No. | System Pressure (torr) | Hot Oil Temperature °C. | Feed Rate (kg/hr) | Distillate Rate (kg/hr) | Distillate to Feed Ratio | Tocopherol Yield to Residue % |
|---|---|---|---|---|---|---|
| 44 | 0.050 | 239 | 30.7 | 16.4 | 0.53 | 95 |
| 45 | 0.051 | 264 | 60.9 | 35.3 | 0.58 | 98 |
| 46 | 0.099 | 279 | 66.0 | 41.2 | 0.62 | 99 |

TABLE 13

Effect of Temperature and Reflux on Multi-Staged Fractionation of Esterified Canola Distillate

| Reference No. | Top Pressure (torr) | Reboiler Temperature (°C.) | Reflux Ratio | Feed Rate (ml/hr) | Distillate to Feed Ratio | Fatty Acid Yield to Distillate (%) | Tocopherol Yield to Residue (%) |
|---|---|---|---|---|---|---|---|
| 47 | 0.7 | 240 | 0.33 | 300 | 0.366 | 93.9 | 92.4 |
| 48 | 0.7 | 255 | 0.33 | 300 | 0.381 | 96.3 | 91.2 |
| 49 | 0.7 | 270 | 0.33 | 300 | 0.388 | 97.1 | 87.3 |
| 50 | 0.7 | 240 | 1.0 | 300 | 0.342 | 92.6 | 99.6 |
| 51 | 0.7 | 255 | 1.0 | 300 | 0.358 | 94.0 | 99.5 |
| 52 | 0.7 | 270 | 1.0 | 300 | 0.329 | 95.8 | 99.1 |
| 53 | 0.7 | 285 | 1.0 | 300 | 0.370 | 100.0 | 99.6 |
| 54 | 0.7 | 300 | 1.0 | 300 | 0.376 | 100.0 | 99.6 |
| 55 | 0.7 | 255 | 2.0 | 300 | 0.359 | 95.0 | 99.6 |
| 56 | 0.7 | 270 | 2.0 | 300 | 0.374 | 96.5 | 99.4 |
| 57 | 0.7 | 285 | 2.0 | 300 | 0.365 | 97.7 | 99.6 |
| 58 | 0.7 | 300 | 2.03 | 300 | 0.358 | 99.4 | 100.0 |

TABLE 14

Short Path Distillation of Esterified Sunflower from Example 5

| Reference No. | Weight (g) | Tocopherols (g) | Sterols (g) | Sterol Esters (g) | Free Fatty Acid (g) | Monoglycerides (g) | Diglycerides (g) | Triglycerides (g) |
|---|---|---|---|---|---|---|---|---|
| 59 | 196.48 | 7.8 | 0.0 | 0.0 | 163.8 | 1.0 | 4.52 | 0.78 |
| 60 | 255.23 | 2.2 | 0.0 | 51.9 | 2.4 | 0.0 | 1.28 | 122.6 |

TABLE 15

ASPEN ™ Program-Generated Material Balance for Three-Step Recycled Distillation Scheme of Figure 1

| Stream | Mass (g/hr) | Free Fatty Acids (g/hr) | Tocopherols (g/hr) |
|---|---|---|---|
| Fresh Feed | 764 | 260 | 65 |
| Distillate 1 | 280 | 253 | 4.5 |
| Bottoms 1 | 1760 | 498 | 305 |
| Distillate 2 | 1276 | 492 | 244.5 |
| Bottoms 2 | 484 | 6.0 | 60.5 |
| Distillate 3 | 182 | 6.0 | 59.0 |
| Bottoms 3 | 301 | 0.0 | 1.0 |

TABLE 16

Two-Step Distillation of Esterified Soy Deodorizer Distillate

| Reference No. | Stream | Mass (g) | Tocopherol Content (%) | Sterol Content (%) | Sterol Ester Content (%) | Free Fatty Acid Content (%) |
|---|---|---|---|---|---|---|
| esterified soy distillate | feed | 1063.28 | 6.80 | <0.1 | 25.04 | 23.26 |
| 61 | distillate #1 | 348.95 | 0.14 | <0.1 | 0.0 | 69.09 |
| 62 | residue #1 | 714.33 | 10.48 | <0.1 | 36.45 | 0.56 |
| 63 | distillate #2 | 143.63 | 48.01 | 0.64 | 0.20 | 3.85 |
| 64 | residue #2 | 545.55 | 0.5 | <0.1 | 53.82 | 0.66 |

TABLE 17

Two-Step Distillation of Esterified Soy Deodorizer Distillate

| Reference No. | Stream | Mass (g) | Tocopherol Content (%) | Sterol Content (%) | Sterol Ester Content (%) | Free Fatty Acid Content (%) |
|---|---|---|---|---|---|---|
| esterified soy distillate | feed | 628.74 | 6.80 | <0.1 | 25.04 | 23.26 |
| 65 | distillate #1 | 260 | 12.25 | <0.1 | 0.0 | 53.37 |
| 66 | residue #1 | 368.74 | 3.15 | <0.1 | 43.95 | 0.0 |
| 67 | distillate #2 | 192.9 |  | <0.1 | 0.0 | 69.52 |
| 68 | residue #2 | 64.4 | 45.75 | 0.47 | 0.0 | 0.0 |

TABLE 18

Two-Step Distillation of Esterified Canola Oil Distillate

| Reference No. | Stream | Mass (g) | Tocopherol Content (%) | Sterol Content (%) | Sterol Ester Content (%) | Free Fatty Acid Content (%) |
|---|---|---|---|---|---|---|
| esterified canola distillate | feed | 780.93 | 5.9 | 0.9 | — | 32.8 |
| 69 | distillate #1 | 409.3 | 9.5 | 0.7 | 0.003 | 62.15 |
| 70 | residue #1 | 367.78 | 2.0 | 0.2 | 65.9 | 0.0 |
| 71 | distillate #2 | 307.6 | 1.8 | <0.1 | 0.0 | 79.4 |
| 72 | residue #2 | 86.24 | 35.0 | 0.1 | 0.6 | 5.3 |

We claim:

1. A method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides; and (b) followed by subjecting said mixture to a series of distillation operations comprising:

(i) one or more separate distillation operations, wherein said distillation(s) is (are) conducted at a temperature of about 200° C. to 320° C. and a pressure of about 0.01 torr to 10 torr, in series wherein unreacted fatty acids and low-boiling components are removed as a vapor effluent and a liquid effluent comprised of tocopherols is removed; and (ii) wherein said liquid effluent from step (b)(i) is subjected to one or more distillations in series, wherein said distillation(s) is (are) conducted at a temperature of about 170° C. to 270° C. and a pressure of about 0.005 torr to 2 torr, wherein a tocopherol concentrate is removed as a vapor effluent and wherein a liquid effluent comprised of sterol esters, fatty acid esters, glycerides, waxes, and other high-boiling substances is removed.

2. The method of claim 1, wherein step (a) is conducted at a temperature of about 150° C. to 230° C. and a pressure of about 100 torr to 200 torr.

3. The method of claim 1, wherein additional $C_{10}$–$C_{22}$ fatty acids are added to the vegetable oil by-product utilized in step (a).

4. The method of claim 1, wherein an acid catalyst is utilized in step (a).

5. The method of claim 4, wherein the acid catalyst is selected from the group consisting of alkyl tin compounds, zinc salts of organic acids, zinc oxide, titanium (IV) alkoxides, and mineral acids.

6. A method for preparing a tocopherol concentrate which comprises the steps:

(a) heating a vegetable oil by-product comprised of tocopherols, fatty acids, sterols, sterol esters of fatty acids, and mono-, di-, and triglycerides, said by-product optionally containing added $C_{10}$–$C_{22}$ fatty acids, optionally in the presence of an acid catalyst, at a temperature of about 70° to 300° C. and a pressure of about 50 torr to 760 torr, while continuously removing water formed thereby, to form a mixture comprised of sterol esters, high boiling fatty acid esters, waxes, and glycerides;

(b) followed by subjecting said mixture to distillation at a temperature of about 170° C. to 270° C. and a pressure of about 0.05 to 10 torr, while removing unreacted fatty acids and low-boiling components as a vapor effluent and a liquid effluent comprised of tocopherols;

(c) followed by subjecting the liquid effluent from step (b) to distillation at a temperature of about 230° C. to 300° C. and a pressure of about 0.01 to 5 torr, while removing remaining fatty acids and approximately 5 to 30 percent of total tocopherols as a vapor effluent and a liquid effluent which is a tocopherol-enriched product; and (d) followed by subjecting the liquid effluent from step (c) to distillation at a temperature of about 170° C. to 270° C. and a pressure of about 0.005 to 2 torr, and collection and isolation of a tocopherol concentrate as a vapor effluent.

7. The method of claim 6, further comprising the step of recycling the tocopherols removed as a vapor effluent in step (c) into the step (b) mixture.

8. The method of claim 6, wherein an acid catalyst is utilized in step (a).

9. A method for preparing a tocopherol concentrate which comprises the steps:

(a) heating a vegetable oil by-product comprised of tocopherols, fatty acids, sterols, sterol esters of fatty acids, and mono-, di-, and triglycerides, said by-product optionally containing added $C_{10}$–$C_{22}$ fatty acids, optionally in the presence of an acid catalyst, to a temperature of about 70°–300° C. and a pressure of about 50 torr to 760 torr, to form a mixture comprised of sterol esters, high boiling fatty acid esters, waxes, and glycerides;

(b) followed by subjecting said mixture to distillation at a temperature of about 170° C. to 270° C. and a pressure of about 0.005 to 2 torr, while removing tocopherols, free fatty acids, and low-boiling materials as a vapor effluent;

(c) followed by subjecting the vapor effluent of step (b) to distillation at a temperature of about 230° C. to 300° C. and a pressure of about 0.01 to 5 torr, thereby removing remaining fatty acids and approximately 5 to 30 percent of total tocopherols as a vapor effluent and a liquid effluent which is a tocopherol-enriched product; and (d) followed by subjecting the liquid effluent from step (c) to distillation at a temperature of about 170° C. to 270° C. and a pressure of about 0.05 to 10 torr, while removing unreacted fatty acids and low-boiling components as a vapor effluent and a liquid effluent which is a tocopherol concentrate.

10. The method of claim 9, further comprising the step of recycling the vapor effluent from step (c) into the step (b) mixture.

11. The method of claim 9, wherein an acid catalyst is utilized in step (a).

12. A method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:
a first distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr,
wherein a vapor effluent which is comprised of free fatty acids and low-boiling materials is removed; and
wherein a liquid effluent which is comprised of a tocopherol-enriched mixture is removed;

(c) followed by feeding the liquid effluent from step (b) to a second distillation zone comprising:
one or more separate distillation apparatus in series selected from the group consisting of a short path evaporator, a wiped film evaporator, a centrifugal molecular still, and a falling film evaporator, operated at a temperature of about 200° C. to 320° C. and a pressure of about 0.01 torr to 10 torr,
wherein a liquid effluent comprised of sterol esters, fatty acid esters, glycerides, waxes, and other high-boiling materials is removed;
wherein a vapor effluent which is a tocopherol concentrate is removed and isolated.

13. The method of claim 12, wherein additional $C_{10}$–$C_{22}$ fatty acids are added to the vegetable oil by-product utilized in step (a).

14. The method of claim 12, wherein step (a) is conducted at a temperature of about 150° C. to 230° C. and a pressure of about 100 torr to 200 torr; step (b) is conducted at a temperature of about 260° C. to 290° C., a pressure of about 0.5 to 4 torr, and a reflux ratio of 0.5 to 2.0; and step (c) is conducted at a temperature of about 200° C. to 250° C. and a pressure of about 0.01 to 0.05 torr.

15. The method of claim 12, wherein an acid catalyst is utilized in step (a).

16. A method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:
one or more separate distillation apparatus in series selected from the group consisting of a short path evaporator, a wiped film evaporator, a centrifugal molecular still, and a falling film evaporator, said apparati operated at a temperature of about 200° C. to 320° C. and a pressure of about 0.01 torr to 10 torr,
wherein a liquid effluent comprised of sterol esters, fatty acid esters, glycerides, waxes, and other high-boiling materials is removed; and
wherein a vapor effluent comprised of a tocopherols, free fatty acids and low-boilers is removed;

(c) followed by feeding the vapor effluent from step (b) to a second distillation zone comprising:
a distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids, and low-boiling materials is removed;

wherein a liquid effluent which is a tocopherol concentrate is removed and isolated.

17. The method of claim 16, wherein step (a) is conducted at a temperature of about 150° C. to 230° C. and a pressure of about 100 torr to 200 torr.

18. The method of claim 16, wherein additional $C_{10}$–$C_{22}$ fatty acids are added to the vegetable oil by-product utilized in step (a).

19. The method of claim 16, wherein step (b) is conducted at a temperature of about 200° C. to 250° C. and a pressure of about 0.01 to 0.05 torr.

20. The method of claim 16, wherein step (c) is conducted at a temperature of about 260° C. to 290° C., a pressure of about 0.5 to 4 torr, and a reflux ratio of about 0.5 to 2.0.

21. The method of claim 16, wherein step (a) is conducted at a temperature of about 150° C. to 230° C. and a pressure of about 100 torr to 200 torr; step (b) is conducted at a temperature of about 200° C. to 250° C. and a pressure of about 0.01 to 0.05 torr; and step (c) is conducted at a temperature of about 260° C. to 290° C., a pressure of about 0.5 to 4 torr, and a reflux ratio of about 0.5 to 2.0.

22. The method of claim 14, wherein an acid catalyst is utilized in step (a).

23. The method of claim 14, wherein the acid catalyst is selected from the group consisting of alkyl tin compounds, zinc salts of organic acids, zinc oxide, titanium (IV) alkoxides, and mineral acids.

24. The method of claim 14, wherein the acid catalyst is selected from the group consisting of butyl stannoic acid, zinc acetate, phosphoric acid, and dibutyl tin oxide.

25. A method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:
a first distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr,
wherein a vapor effluent comprised of a substantial fraction of the unreacted free fatty acids, and low-boiling materials is removed,
wherein a liquid effluent which is comprised of a tocopherol-enriched mixture is removed;

(c) followed by feeding the liquid effluent from step (b) to a second distillation zone comprising:
a second distillation apparatus selected from the group consisting of a short path evaporator, a wiped film evaporator, a centrifugal molecular still, and a falling film evaporator, operated at a about 240° C. to 280° C. and a pressure of 0.01 to 2 torr,
wherein a vapor effluent comprised of remaining fatty acids and approximately 5 to 30 percent of total tocopherols is removed,
wherein a liquid effluent comprised of a tocopherol-enriched mixture is removed; and (d) followed by feeding the liquid effluent from step (c) to a third distillation zone comprising:
a third distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr,
wherein a vapor effluent which is a tocopherol concentrate is removed and isolated.

26. The method of claim 25, wherein step (a) is conducted at a temperature of about 150° C. to 230° C. and a pressure of about 100 torr to 200 torr.

27. The method of claim 25, wherein additional $C_{10}$–$C_{22}$ fatty acids are added to the vegetable oil by-product utilized in step (a).

28. The method of claim 25, wherein step (b) is conducted at a temperature of about 200° C. to 240° C. and a pressure of about 0.5 to 4 torr.

29. The method of claim 25, wherein step (c) is conducted at a temperature of about 240° C. to 280° C. and a pressure of about 0.1 to 2 torr.

30. The method of claim 25, wherein step (d) is conducted at a temperature of about 200° C. to 240° C. and a pressure of about 0.01 to 0.05 torr.

31. The method of claim 25, wherein step (a) is conducted at a temperature of about 150° C. to 230° C. and a pressure of about 100 torr to 200 torr; step (b) is conducted at a temperature of about 200° C. to 240° C. and a pressure of about 0.5 to 4 torr; step (c) is conducted at a temperature of about 240° C. to 280° C. and a pressure of about 0.1 to 2 torr; and step (d) is conducted at a temperature of about 200° C. to 250° C. and a pressure of about 0.01 to 0.05 torr.

32. The method of claim 25, wherein tocopherols and fatty acids removed as a vapor effluent in step (c) are recycled into the step (b) mixture.

33. The method of claim 25, wherein an acid catalyst is utilized in step (a).

34. The method of claim 25, wherein the acid catalyst is selected from the group consisting of alkyl tin compounds, zinc salts of organic acids, zinc oxide, titanium (IV) alkoxides and mineral acids.

35. The method of claim 34, wherein the acid catalyst is selected from the group consisting of butyl stannoic acid, zinc acetate, zinc oxide, phosphoric acid, titanium tetraisopropoxide and dibutyl tin oxide.

36. A method for preparing a tocopherol concentrate which comprises the steps:

(a) heating a vegetable oil by-product comprised of tocopherols, fatty acids, hydrocarbons, sterol esters of fatty acids, sterols, triterpenoid alcohols, methyl-sterols, and mono-, di-, and triglycerides, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:
a first distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr,
wherein a vapor effluent comprised of tocopherols, unreacted free fatty acids, and low-boiling materials is removed, (c) followed by feeding the vapor effluent from step (b) to a second distillation zone comprising:
a second distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr,
wherein a vapor effluent comprised of a substantial fraction of the unreacted free fatty acids, and low-boiling materials is removed, and
wherein a liquid effluent which is a tocopherol concentrate is removed and isolated; and
(d) followed by feeding the liquid effluent from step (c) to a third distillation zone comprising:
a third distillation apparatus selected from the group consisting of a short path evaporator, a wiped film evaporator, a centrifugal molecular still, and a falling film evaporator, operated at a about 240° C. to 280° C. and a pressure of 0.01 to 2 torr,
wherein a vapor effluent comprised of remaining fatty acids and approximately 5 to 30 percent of total tocopherols is removed,
wherein a vapor effluent which is a tocopherol concentrate is removed and isolated.

37. The method of claim 36, wherein step (a) is conducted at a temperature of about 150° C. to 230° C. and a pressure of about 100 torr to 200 torr.

38. The method of claim 36, wherein additional $C_{10}$–$C_{22}$ fatty acids are contacted with the vegetable oil by-product utilized in step (a).

39. The method of claim 36, wherein step (b) is conducted at a temperature of about 200° C. to 240° C. and a pressure of about 0.01 to 0.05 torr.

40. The method of claim 36, wherein step (c) is conducted at a temperature of about 200° C. to 240° C. and a pressure of about 0.5 to 4 torr.

41. The method of claim 36, wherein step (d) is conducted at a temperature of about 240° C. to 280° C. and a pressure of about 0.1 to 2 torr.

42. The method of claim 36, wherein step (a) is conducted at a temperature of about 150° C. to 230° C. and a pressure of about 100 torr to 200 torr; step (b) is conducted at a temperature of about 200° C. to 240° C. and a pressure of about 0.01 to 0.05; step (c) is conducted at a temperature of about 200° C. to 240° C. and a pressure of about 0.5 to 4 torr; and step (d) is conducted at a temperature of about 240° C. to 280° C. and a pressure of about 0.1 to 2 torr.

43. The method of claim 36, wherein tocopherols and fatty acids removed as a vapor effluent in step (d) are recycled into the step (b) mixture.

44. The method of claim 36, wherein tocopherols and fatty acids removed as a vapor in step (d) are recycled into the step (c) mixture.

45. The method of claim 36, wherein an acid catalyst is utilized in step (a).

46. The method of claim 45, wherein the acid catalyst is selected from the group consisting of alkyl tin compounds, zinc salts of organic acids, titanias, and mineral acids.

47. The method of claim 45, wherein the acid catalyst is selected from the group consisting of butyl stannoic acid, zinc acetate, zinc oxide, phosphoric acid, and dibutyl tin oxide.

* * * * *